United States Patent [19]
Pitesky

[11] Patent Number: 5,673,705
[45] Date of Patent: Oct. 7, 1997

[54] INJECTION PICK HOLDER APPARATUS

[76] Inventor: Isadore Pitesky, 4001 Linden Ave., Long Beach, Calif. 90807

[21] Appl. No.: 705,632

[22] Filed: Aug. 30, 1996

Related U.S. Application Data

[62] Division of Ser. No. 352,364, Dec. 9, 1994, Pat. No. 5,551,441.

[51] Int. Cl.⁶ .................................................. A61B 5/00
[52] U.S. Cl. ............................................................. 128/743
[58] Field of Search .................................. 128/743; 604/46, 604/47; 206/363–366, 569–572; 24/498, 499, 504, 547

[56] References Cited

U.S. PATENT DOCUMENTS

| | | | |
|---|---|---|---|
| 3,289,670 | 12/1966 | Krug et al. | 128/743 |
| 3,556,080 | 1/1971 | Hein | 128/743 |
| 3,896,527 | 7/1975 | Miller et al. | 24/499 |
| 4,292,979 | 10/1981 | Inglefield et al. | 128/743 |
| 5,147,306 | 9/1992 | Gubich | 24/498 |

*Primary Examiner*—Max Hindenburg
*Attorney, Agent, or Firm*—Fulwider Patton Lee & Utecht, LLP

[57] ABSTRACT

An injection vial holder apparatus to releasably hold and apply to a patient a plurality of allergen testing applicators of the type stored in a tray of upstanding posts arrayed in a predetermined pattern. The holder includes a block member with longitudinal slits defining hinged flanking strips and further includes opposing clamp jaw segments which close onto the respective posts. A pair of hand grasp ears project upwardly along the opposite sides of the block to be grasped and thereby pivoting the flanking strips about the hinge to expand the clamp jaws for application of the allergen testing applicators. An elastic band is used to surround the strips and contract the clamp jaws.

13 Claims, 2 Drawing Sheets

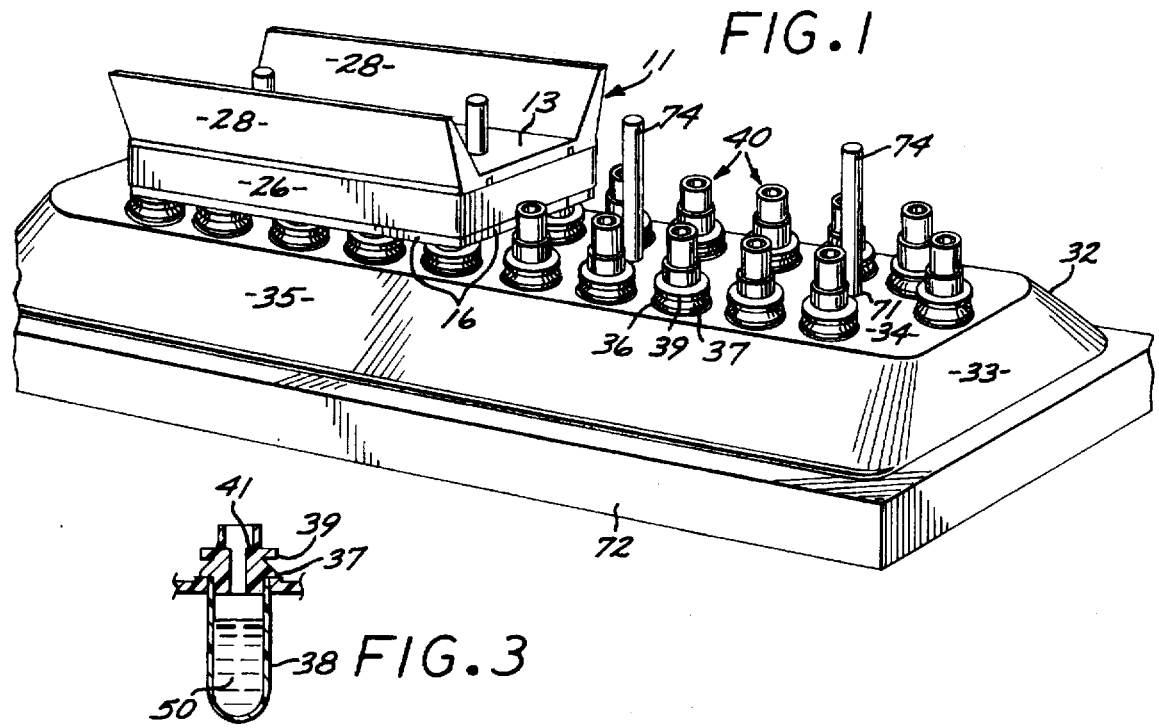
FIG. 1
FIG. 3
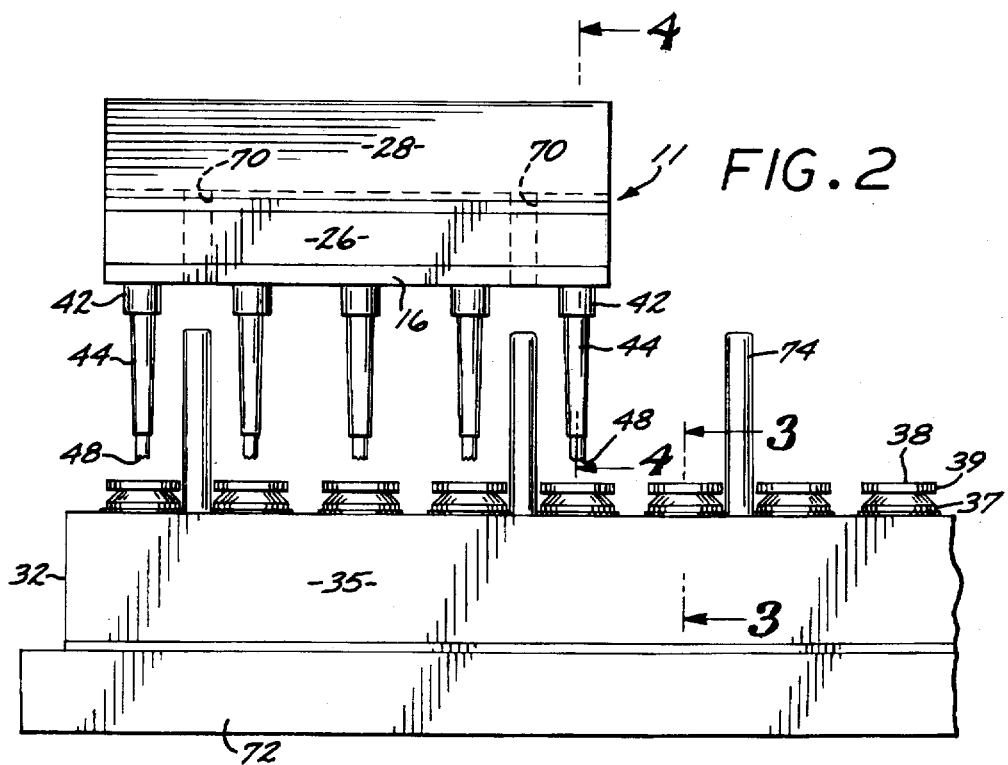
FIG. 2

INJECTION PICK HOLDER APPARATUS

This is a divisional application of U.S. application Ser. No. 08/352,364 filed on Dec. 9, 1994 and now U.S. Pat. No. 5,551,441.

BACKGROUND OF THE INVENTION

1. Field of the Invention:

The present invention relates to allergy testing and, more particularly, to an apparatus that allows for simultaneously testing a patient's reaction to a plurality of allergens.

2. Description of the Prior Art:

Allergy testing involves subjecting a patient to a wide variety of different allergens to determine which allergens cause an allergic reaction in the patient. Such testing requires that the respective allergens be applied beneath the surface of the patient's skin. One conventional method is to individually place a drop of allergen on the patient's skin and then prick the contacted skin so that the allergen will be delivered under the patient's skin. For this purpose portable trays have been employed incorporating upwardly opening wells spaced thereabout for receipt of tubular shaped vial tubes for holding respective allergens for receipt of individual vial applicators or picks. A device of this type is shown in my U.S. Pat. No. 4,237,906. This procedure is very time consuming, expensive and, in many instances, subjects the patient to prolonged periods of uneasiness and discomfort.

Another method employed in the prior art is to simultaneously apply a plurality of allergens to a patient. Forms of such apparatus can be found in U.S. Pat. Nos. 4,292,979 and 5,154,181.

The above-mentioned prior art apparatus have some disadvantageous features associated with them. For example, one of the prior art references, mentioned in U.S. Pat. No. 5,154,181, has the respective applicator picks fixedly attached to the hand held applicator member of the device. As such, the hand held applicator applies only a preset number of allergens and is not readily adaptable for use in applying different sets of allergens. In addition, the entire applicator device must be sterilized between use thereof, which is an inefficient and time-consuming process.

The other prior art reference, set forth in U.S. Pat. No. 4,292,979, permanently attaches the applicator needles to the hand held applicator by means of machine screws which threadably engage such needles. As such, the needles are not readily exchangeable to provide sets of different desired members of applicators. Another such applicator is one sold by Lincoln Diagnostics Inc., Decater, Ill. under the trade designation MULTI-TEST as shown at 30 USPQ2d 1817 and at 1821 (U.S. TTAB), U.S. Pat. No. 3,556,080. The devices shown are in the form of plastic frames formed with laterally disposed legs terminating in spaced apart feet defining respective points disposed in a common plane for receipt of respective allergens to be simultaneously applied to a patient. As with the above mentioned applicator, these devices suffer the shortcoming that there are a fixed number of pricks thus subjecting each patient on which they are used to a fixed number of pricks irrespective of the number of allergens to be applied. Therefore, the hand held applicators of the prior art references do not provide an efficient arrangement for engaging and applying multiple sets of allergens to a patient. In addition, due to the fact that removing the needles is quite time-consuming in the prior art references, those testing devices are essentially established with respect to the number of needles they may apply to a patient, so that the testing surface, namely the patient's skin, becomes a factor in the accurate application of the allergens. Further, there is no provision for varying the number of allergens to be applied so that, without the time-consuming procedure of manually removing the individual unwanted applicator needles, each patient will be exposed to the same preset number of needle pricks irrespective of the number of allergens to be applied.

As such, it may be appreciated that there continues to be a need for an improved allergen testing device that allows for simultaneous application of a plurality of allergens while allowing the operator to apply different sets of injection picks to the patient with the same testing device without the need for sterilization of the device between successive uses thereof. In addition, there continues to be a need for a device which limits the amount of waste materials created by the use thereof, as well as for a device which allows the operator to efficiently vary the number of allergens to be applied to different patients. The instant invention addresses such needs.

SUMMARY OF THE INVENTION

Briefly, and in general terms, the present invention comprises an injection vial holder for use in holding and applying to a patient a plurality of allergen testing applicator picks normally stored in a tray. The vial tray includes a plurality of nesting bores into which are slidably received and contained, respective upwardly opening vial receptacle tubes. The vial tray tubes telescopically receive the respective elongated injection picks therein. The nesting bores are typically formed in spaced relation on the tray in two longitudinal rows. The pick holder block is formed with at least one longitudinal slit extending upwardly from the bottom to, in one embodiment, stop just short of the upper surface to leave a live hinge. As such, the slit partitions the block into flanking strips into which is formed a plurality of longitudinally spaced apart, downwardly opening bores defining respective pairs of clamp jaws disposed in spaced relation in accordance with the spacing of the vial receptacle tubes held in the vial tray for, when such jaws are open, sliding downward over the respective top ends of picks inserted in such vials. A pair of upwardly and outwardly diverging hand grasp ears extend away from the upper surface of the block to allow an operator to grasp and squeeze such hand grasp ears. Such squeezing together of the ears will serve to force the flanking side strips to pivot outwardly and away from the center strip, thereby expanding the clamp jaws so that the lower end assumes an open position thereby serving to release any picks held by such clamp jaws. An elastic band may encompass the peripheral side walls to enhance the tendency to compress the clamp jaws against the opposite sides of the clamp posts in such picks to thereby provide for secure gripping thereof as the holder transports them from the tray for application to the skin of a patient.

DESCRIPTION OF THE DRAWINGS

FIG. 1 is a perspective view of a pick holder and tray apparatus embodying the present invention;

FIG. 2 is a partial front view, in enlarged scale, of the pick holder shown in FIG. 1 removed from its seated position on the vial tray and carrying a plurality of picks;

FIG. 3 is a vertical sectional view, in enlarged scale, taken along the line 3—3 of FIG. 2;

FIG. 4 1s a vertical sectional view taken along the line 4—4 of FIG. 2;

DETAILED DESCRIPTION OF THE PREFERRED EMBODIMENT

Figure 4:
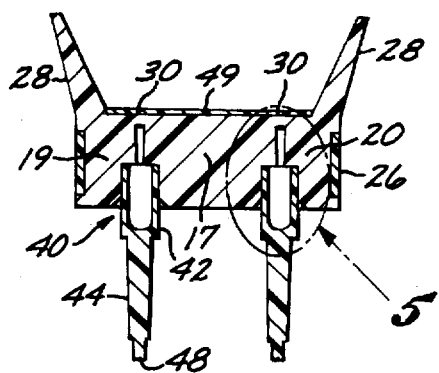
Figure 5:
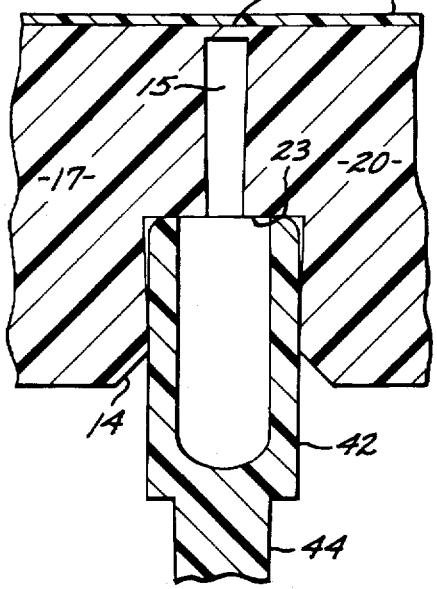
FIG. 5 is a detailed sectional view, in enlarged scale, taken of the area 5 of FIG. 4.
Figure 6:
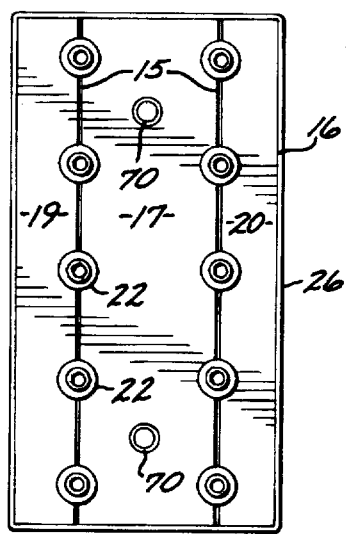
FIG. 6 is a bottom plan view of the holder shown in FIG. 2.
Figure 7:
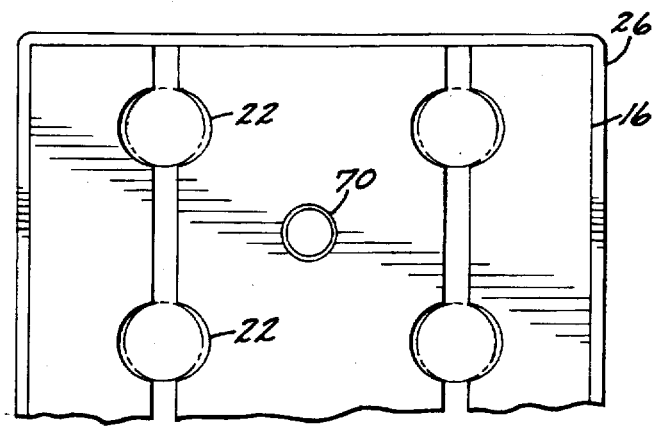
FIG. 7 is a partial bottom plan view, in enlarged scale, of the holder shown in FIG. 7 but expanded to its open position.
Figure 8:
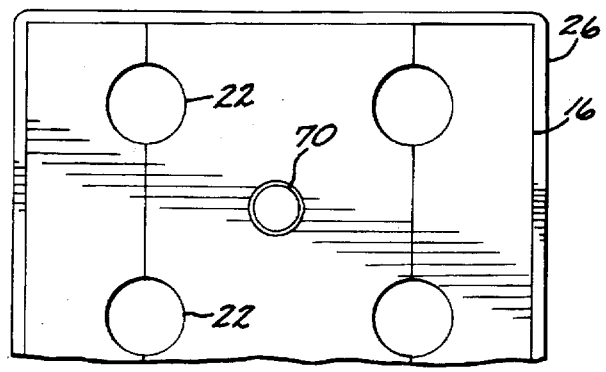
FIG. 8 Is a partial bottom plan view similar to FIG. 7 but showing the holder in its closed position.

In the following detailed description, like reference numerals will be used to refer to like or corresponding elements in the different figures of the drawings. Referring to FIG. 1, the vial tray 32 is constructed of a polymerized resin and is in the form of a hollow truncated pyramid defining a top plate 34 having formed thereon a plurality of bores 36 formed in spaced relation into which are placed respective upwardly opening vial receptacle tubes 38 (FIG. 3). The vial receptacle tubes contain therein respective allergens 50 (FIG. 3) and further receive telescopically in the respective tops thereof applicators in the form of applicator picks, generally designated 40 (FIG. 1). An injection vial holder, generally designated 11, includes a rectangular block 13 of resilient material formed with a pair of longitudinal laterally spaced apart downwardly opening slits 15 which serve to partition such block into a center strip 17 and oppositely disposed flanking side strips 19 and 20 (FIGS. 6, 7 and 8). The block material immediately above the top ends of the respective slits defines respective living hinges 30 to allow the flanking side strips to pivot slightly outwardly and upwardly with respect to the center strip (FIGS. 4 and 5). Formed in spaced relation along each of the longitudinal slits are upwardly and inwardly tapered, downwardly opening jaw sockets 22 having respective diameters smaller than that of the picks to define oppositely disposed semi-circular jaws to be received in telescopical relation over the top ends of the respective picks as the holder is moved downwardly thereover. Surmounted on the opposite sides of the flanking strips 19 and 20 are upwardly and outwardly angling segments defining hand grasp ears 28 to be grasped at the respective top extremities by a technician to be drawn inwardly to thereby apply an expansive force to such flanking strips causing them to pivot upwardly and outwardly to open the longitudinal slits 15 and consequently open the sockets 22 as shown in FIG. 7 for telescopical receipt of such picks as shown in FIG. 1. An elastic band 26 encompasses the peripheral walls of the holder block 13 to urge the flanking strips 19 and 20 laterally inwardly to press the opposite sides of the sockets 22 inwardly against the opposite side of the picks to thus grip such picks so they will be securely held therein.

Referring to FIGS. 2 and 6 the block 13 further has formed thereon a plurality of block alignment bores 70 formed in spaced relation and interposed between the respective longitudinal slits. 15 in a longitudinal row to telescopically receive therein alignment means to properly align the block with the vial tray 32 as described hereinafter.

The vial tray 32 may be molded from a lightweight material such as a polymerized resin. The tray is formed with the top wall 34, oppositely disposed, downwardly and outwardly inclined side walls and end walls 35 and 33, respectively (FIG. 1). The tube bores 36 are conveniently formed at their respective peripheries with upwardly projecting annular stand-off rings 37 to hang the respective vials therefrom (FIG. 3). The vial tray further has formed thereon a single row of longitudinally spaced apart alignment bores 71 interposed between the longitudinal rows of nesting bores 36. A base plate 72 is provided for nesting of the tray thereon and is formed with a plurality of upstanding alignment rods 74 arranged in longitudinal spaced relation and projecting upwardly beyond the horizontal plane of the top ends of the vial ports for slip fit receipt in the alignment bores 71 and the block alignment bores 70 formed on the holder block. As such the vial tray may be aligned over the base and slidably extended downwardly thereon. With the vial tray seated on the base the alignment rods project upwardly through the top wall 34 (FIGS. 1 and 2) so that the block alignment bores may be aligned thereover to, when such block is properly aligned thereover, telescopically accept the alignment rods therein and as such maintain the pick holder aligned with the vial tray so that the picks 40 are slidably received into the respective sockets 22 so that the vial tray, holder, and base are releasably connected to provide for ease of transporting the device and convenience of use.

The vial receptacle tubes 38 may be formed from a suitable transparent or translucent plastic material, glass, or the like, and serve to hold therein the desired quantities of various liquid allergens 50 which are to be applied to a patient undergoing an allergy test (FIG. 3). The vial receptacle tubes are generally cylindrical and are open at the respective top ends (FIG. 3) to telescopically accept applicator picks 40 therein (FIG. 1). The vial receptacle tubes are further formed with radially outwardly flared annular flanges defining stop rings 39 thereon, adjacent the upper ends thereof, to overlie the respective stand off rings 37 to define stops for suspension of the respective vial receptacle tubes (FIG. 1). The picks are formed integrally at their upper extremities with upstanding cylindrical clamp posts 42 projecting upwardly above the stop rings 39 to be slidably received in the respective sockets 22 when open. Such posts are preferably rounded at their top ends to facilitate receipt in the holder. Such picks are formed below such rings 39 with downwardly depending elongated stems 44 tapering downwardly and inwardly to terminate in respective penetration points 48 configured to be normally immersed in the respective allergens 50 and formed with sharp edges to pierce the skin of the patient upon application thereto (FIG. 2). The vial receptacle tubes are further formed with radially inwardly flared annular shoulders 41 to define seats on which the lower ends of the cylindrical clamp posts rest so that the stems and penetration points project downwardly therefrom and are immersed in the respective allergens.

The respective sockets 22 are preferably formed with circular cross sections to define oppositely disposed jaws configured to, when closed, accept and securely grip the opposite sides of the cylindrical clamp posts 42 of the applicator picks 40. Referring to FIG. 5, the sockets 22 terminate at their respective lower ends in frusto conical funnel shaped mouths 14 to serve in guiding the injection vial posts into the respective sockets. The respective sockets 22 are further formed having uniform, predetermined depths and terminate in respective top ends 23 (FIG. 5) so that the top ends of the respective clamp posts 42 will abut thereagainst to maintain the respective points 48 disposed in a common plane to be simultaneously pressed against the skin of a patient.

In the preferred embodiment, a one sided adhesive strip of polyethylene 49 is adhered to the top wall of such holder to act as a hinge reinforcing plate. Thus, such plate 49 will provide a flexible member operative to reinforce the living hinges 30 or, in the event the web defining such hinges breaks or is cut through, serve as the primary hinge element. As will be apparent to those of skill in the art, the holder 11 may be made of any one of a number of materials such as wood or plastic, for example Lucite, and the hinge plate 99 attached to act as the hinging element.

The hand grasp ears 28 are formed as an integral segment of the holding block 13 and extend from the upper surface of the block in the preferred upwardly and outwardly angling configuration shown in FIG. 1. The hand grasp ears have such a configuration for ease of handling the holding block as well as for ease of applying the compressive force to the hand grasp ears which drives such ears toward one another. Such squeezing together of the hand grasp ears will serve to force the lower ends of the flanking side strips 19 and 20 to pivot outwardly and upwardly away from the center strip 17, thus forcing the respective sockets 22 to be expanded to assume their open positions (FIG. 7).

In the preferred embodiment the elastic band 26 encompasses the peripheral side walls 16 of the block 13 (FIG. 1) to compress the flanking strips laterally inwardly. The elastic band is formed with a relaxed circumference smaller than the perimeter of the holder body so that it will be securely held in place to apply a contracting bias. As such, the elastic band will continually be in tension when it is in place encompassing the peripheral side walls and hand grasp ears. Such force will tend to force the lower ends of the flanking side strips 19 and 20 to pivot inwardly and contact the center strip 17 thereby serving to contract the respective sockets so that they assume their closed positions to securely grip the clamp posts 42 of the applicator picks 40 (FIG. 8). Although an elastic band is incorporated in the preferred embodiment, it will be appreciated that other suitable means of biasing the flanking strips may be employed. For example, the parent material for the holder may be constructed of resilient material to provide an inherent bias or a return spring may be interposed between the hand grasp ears to bias the top of such ears outwardly. As such, when the hand grasp ears are released, the return spring will serve to drive the respective hand grasp ears away from one another thereby applying a compressive force to the lower portion of the block which will serve to close the respective sockets 22.

While the specific dimensions are not critical to the invention, in the preferred embodiment, the block 13 may have overall dimensions of about 3½" in length, 1½" in width, and ⅝" in height. The longitudinal slits 15 intrude substantially 19/32" through the block and are further formed 5/16" from the outer edges of the block and are spaced 1" apart in parallel configuration from each other. The clamp jaws 22 have cross-sectional longitudinal diameters of 3/16" and intrude into the block ⅜" and further are formed in spaced relation along the respective slits at intervals of ¾". The frusto conical orifices 23 of the clamp jaws terminate at the lower end with diameters of substantially 5/16". The hand grasp ears 28 extend perpendicularly from the upper end for substantially 5/16" and then angle outwardly at an angle of substantially 30 degrees and further extend ½". The elastic band 26 has a circumference of substantially 7½", a width of ½", and a thickness of about 1/16". The vial tray 32 has an overall length of substantially 8", a width of 3", and a height of 1". The tube bores 36 have cross-sectional diameters of ⅜" and are spaced ¾" from one another along the longitudinal rows in accordance with the clamp jaws formed on the injection vial holder. The longitudinal rows on the vial tray are spaced 1" from each other, likewise in accordance with the longitudinal slits formed on the injection vial holder. The vial receptacle tubes 38 are 1¼" long and ⅜" in diameter. The injection picks 40 have clamp posts 42 of substantially ⅝" in height and stems 44 that extend 1" in length.

In operation, the injection pick holder 11, vial tray 32, and base plate 72 of the present invention may be conveniently stored together or separately during non-use thereof due to their relatively small size and may easily and quickly be retrieved for immediate use thereof. Commonly used allergens 50 may be stored in the vial tubes 38 and/or the selected ones of such tubes may be filled with the allergens selected for the particular patient. In either event the allergens may be selected and the particular vials filled prior to the time the patient is to be tested. Assuming the selected vial tubes have been filled and the picks 40 to act as the skin pricking elements have been placed in such selected tubes, the operator may grasp the injection vial holder by means of the outwardly angling segments of the hand grasp ears 28 to transport it to a position directly above the vial tray 32. The operator may then manually squeeze the hand grasp ears toward one another. Such squeezing together of the hand grasp ears will serve to draw the top of such ears inwardly toward one another thus pivoting outwardly the lower ends of the flanking side strips 19 and 20 from the center strip 17 to expand the longitudinal slits 15 and thus the respective pairs of clamp jaws defining the respective sockets 22 to open such jaws to the position shown in FIG. 7. The operator may then lower the pick holder to telescopically receive the respective alignment rods 74 in the respective block alignment bores 70 to thereby assure proper alignment of the injection vial holder with the vial tray. Further downward movement of the holder onto the vial tray serves to project the respective clamp posts 42 upwardly into the respective downwardly open sockets 22 until the top ends of such posts abut against the top ends 23 of the respective sockets (FIGS. 4 and 5). The operator may then release the hand grasp ears to allow the elastic band 26 to draw the respective flanking side strips 19 and 20 laterally inwardly toward the center strip 17. This serves to rotate the respective clamp jaws to their respective closed positions gripping the diametrical opposite sides of the clamp posts 42. The operator may then raise the injection vial holder 11 from the vial tray 32 to thereby bodily lift all the injection vials onto which the jaws have clamped. The operator may then transport the injection vial holder to the patient and simultaneously apply the plurality of allergens to the patient's skin by pressing the penetration points 48 directly thereto in unison.

When the application of the allergens to the skin of the patient has been performed, the pick holder 11 may either be actuated to release the picks for disposal thereof (FIG. 1). Assuming the picks are replaced in the vial tubes 38, the operator may then once again squeeze together the hand grasp ears 28 which will serve to expand the pairs of clamp jaws to spread the respective sockets 22 (FIG. 7). The injection pick holder may then be elevated from the vial tray with the picks 40 remaining housed in the respective vial receptacle tubes 38 on the vial tray 32. If the patient requires more testing, the pick holder is ready to engage and apply to the patient a different set of picks. If the patient has completed his or her testing, the pick holder, vial tray and base may be stored separately or together until they are needed again. Because the pick holder does not come into contact with the patient directly, it will not need to be sterilized and will be readily reusable with multiple additional sets of picks.

Figure 9:
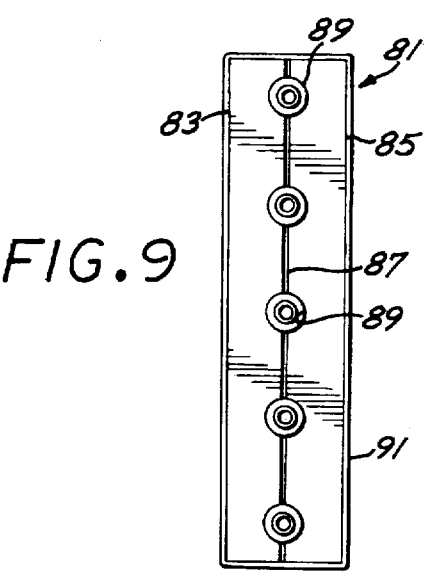
FIG. 9 is a bottom plan view of a holder incorporated in a second embodiment of the apparatus of the present invention.

The embodiment of my injection vial holder apparatus shown in FIG. 9 is similar to that shown in FIGS. 1 through 8, except that it includes a holder, generally designated 81, in the form of a pair of flanking strips 83 and 85 separated by a longitudinal slot 87 having vial sockets 89 spaced longitudinally therealong to define gripping jaws. An elastic biased band 91 surrounds the strips 83 and 85 to bias such strips together in a manner described hereinabove.

Thus, the holder shown in FIG. 9 operates in substantially the same manner as the holder shown in FIGS. 1 through 8 and may be utilized with, for instance, a row of picks carried in the holder tray shown in FIG. 1. As will be understood by those skilled in the art, a single row holder of this type overcomes what is sometimes referred to as a geometric error when applied to smaller diameter arms. That is, it eliminates the necessity of maneuvering the older in effort to first prick one longitudinal area of a small diameter arm with one row of pricks and then roll the holder about its longitudinal center line to price another longitudinal area of the arm with a second row of picks.

From the foregoing, it will be appreciated that the injection vial holder apparatus of the present invention provides a convenient, convertible, and readily reusable device of relatively simple construction which results in the saving of considerable material costs. The device provides the operator with the ability to quickly and easily apply numerous types of allergens to a particular patient and further does not require; sterilization between successive uses thereof. The device does not require the application of allergen to each individual applicator immediately before performing an allergen test which saves time as well as expensive testing materials. In addition, the device limits the amount of infected material which must be disposed of, thereby reducing operating costs. Furthermore, adequate spacing between testing sites on a patient's skin is maintained by the spaced apart configuration of the respective sockets on the applicator pick holder. Finally, the relatively sturdy construction provides for a long useful life thereof.

While particular forms of the invention have been illustrated and described, it will also be apparent that various modifications can be made without departing from the spirit and scope of the invention. Accordingly, it is not intended that the invention be limited, except as by the appended claims.

What is claimed is:

1. An allergen applicator apparatus for releasably holding and applying to a patient a plurality of allergen testing applicator picks of the type stored in a tray to be held with respective upstanding posts arrayed in a predetermined pattern and comprising:

an elongated block member formed with at least one downwardly opening longitudinal slit to define flanking strips and including at the top end of said slit a hinge for pivoting of said strips outwardly and upwardly and further a plurality of pairs of opposing clamp jaw segments in a predetermined pattern along the slit and operable to receive the respective said posts and closeable into gripping relation on the respective said posts;

a pair of oppositely disposed hand grasp ears projecting upwardly from the opposite sides of said block to be grasped at the top ends and drawn together to pivot said strips about said hinge to expand said clamp jaws segments; and a biasing device to bias said strips together to contract said jaw segments toward one another.

2. The apparatus of claim 1 for use with said applicators held in a tray disposed in spaced relation along a pair of coextensive rows and further including:

a pair of said longitudinal slits formed in laterally spaced apart parallel configuration to form a central and two flanking strips and including at the top of each slit a hinge; and a plurality of pairs of clamp jaw segments formed in spaced relation along said slits for clamping receipt of said rows of posts.

3. The apparatus of claim 1 wherein:
said block member is formed of polypropylene.

4. The apparatus of claim 1 wherein:
said hand grasp ears are formed with an upwardly and outwardly angling configuration.

5. The apparatus of claim 1 wherein:
said allergen applicator apparatus is formed with a flat top side and said hinge includes a flexible strip mounted on said top side.

6. The apparatus of claim 1 wherein:
said block is constructed of flexible material configured to connect said strips together at said top end of said slit to form a living hinge defining said aforementioned hinge.

7. The apparatus of claim 1 for use with applicator picks having said posts configured in the form of cylindrical posts and wherein:
said snips are formed with pairs of confronting semicylindrical sockets defining said jaw segments configured to grippingly engage the opposite sides of posts.

8. An allergen applicator apparatus for releasably holding the upstanding posts of allergy testing applicator picks positioned in vials stored in spaced relationship in a tray and comprising:

an elongated block member formed with at least one downwardly opening longitudinal slit to define flanking strips and including at the top end of said slit a hinge for pivoting of said strips outwardly and upwardly and further a plurality of opposing clamp jaw segments formed in said spaced relation along said longitudinal slit operable to receive the respective said posts and closeable into gripping relation on the respective said posts;

a resilient band surrounding said block and biasing said strips toward one another; and a pair of oppositely disposed hand grasp ears projecting upwardly from the opposite sides of said block to be grasped at the top ends and drawn together to pivot said strips about said hinge to expand said clamp jaws segments.

9. An allergen applicator apparatus for releasably holding the upstanding posts of a plurality of allergy testing applicator picks and comprising:

an elongated block member formed with at least one downwardly opening longitudinal slit to define flanking strips and including at the top end of said slit a hinge for pivoting of said strips outwardly and upwardly and further a plurality of opposing clamp jaw segments formed in spaced relation along said longitudinal slit operable to receive the respective said posts and closeable into gripping relation on the respective said posts;

a pair of oppositely disposed hand grasp ears projecting upwardly from the opposite sides of said block to be grasped at the top ends and drawn together to pivot said strips about said hinge to expand said clamp jaw segments; and a biasing device on said block member to bias said strips together to contract said clamp jaw segments.

10. An allergen pick holder for setting on the top of an allergen pick and tray apparatus of the type including a tray formed with a plurality of upwardly opening allergen wells receiving applicator picks having respective upstanding holder posts arrayed in a predetermined pattern, said holder comprising:

a first elongated clamp member formed with a plurality of clamp segments disposed in said predetermined pattern and configured with respective laterally opening concavities for engaging the respective one sides of the respective said posts;

a second clamp member adjacent said first clamp member and formed with pairs of clamp segments, confronting the first mentioned clamp segments and configured to cooperate therewith in frictionally clamping onto the respective said posts;

a hinge connecting the top of said clamp members together for pivoting from an open position to a closed position gripping the respective said posts between the respective said clamp segments;

a biasing device biasing said clamp members to said closed position; and a pair of laterally spaced apart hand grasp ears mounted on the respective said clamp members to be grasped and dram together to rotate said first and second clamp members about said hinge to said open position.

11. An allergen pick holder according to claim 10 wherein:

said first and second clamp members are in the form of co-extensive elongated blocks configured with respective pairs of confronting semi-cylindrical sockets.

12. An allergen pick holder according to claim 11 wherein:

said blocks are rigid.

13. An allergen pick holder according to claim 11 wherein:

said blocks are constructed of hard plastic.

* * * * *